United States Patent [19]

Seelich et al.

[11] Patent Number: 5,883,078
[45] Date of Patent: Mar. 16, 1999

[54] HEMOSTYPTIC AND TISSUE ADHESIVE

[75] Inventors: Thomas Seelich, Vienna; Peter Turecek, Klosterneuburg, both of Austria

[73] Assignee: Immuno Aktiengesellschaft, Vienna, Austria

[21] Appl. No.: 661,070

[22] Filed: Jun. 10, 1996

[30] Foreign Application Priority Data

Jun. 12, 1995 [DE] Germany .......................... 195 21 324.6

[51] Int. Cl.$^6$ .......................... A61K 38/00; C07K 14/00
[52] U.S. Cl. .............................. 514/12; 514/21; 530/381; 530/384
[58] Field of Search ...................... 514/12, 21; 530/381, 530/384

[56] References Cited

U.S. PATENT DOCUMENTS

| | | | |
|---|---|---|---|
| 4,427,650 | 1/1984 | Stroetmann | 424/46 |
| 4,442,655 | 4/1984 | Stroetmann | 53/428 |
| 4,453,939 | 6/1984 | Zimmerman et al. | 604/368 |
| 4,948,724 | 8/1990 | Yin | 435/13 |
| 5,407,671 | 4/1995 | Heimburger et al. | 424/94.1 |

FOREIGN PATENT DOCUMENTS

| | | |
|---|---|---|
| 359652 | 2/1979 | Austria . |
| 359653 | 2/1979 | Austria . |
| 369990 | 7/1981 | Austria . |
| 0159311A1 | 10/1985 | European Pat. Off. . |
| 0253198B1 | 1/1988 | European Pat. Off. . |
| 0321442A2 | 6/1989 | European Pat. Off. . |
| 0637451A1 | 8/1994 | European Pat. Off. . |
| 3105624A1 | 9/1982 | Germany . |
| 3214337C2 | 10/1983 | Germany . |
| 4325872C1 | 8/1994 | Germany . |

OTHER PUBLICATIONS

Rosing et al., Thombosis and Haemostatis, 65(5): 627–630 (1991).

Olson et al., Biochimica et Biophysica Acta, 557: 9–23 (1979).

Quick, J. Biol. Chemist, 109: 73–74.

Caplus Abstract No. (1991): 30152 JP 02167234.

*Primary Examiner*—Cecilia J. Tsang
*Assistant Examiner*—Bennett Celsa
*Attorney, Agent, or Firm*—Foley & Lardner

[57] ABSTRACT

A stable tissue adhesive is described which comprises fibrinogen and an activator or pro-activator of prothrombin, wherein its content of prothrombin present in blood is less than 5 units/g fibrinogen. This tissue adhesive can be present as a liquid or dry preparation and can optionally be applied to a biologically degradable water-soluble support.

35 Claims, No Drawings

HEMOSTYPTIC AND TISSUE ADHESIVE

FIELD OF THE INVENTION

The invention relates to a storage-stable, pharmaceutical preparation based on fibrinogen and a coagulation factor activator, for hemostasis, bonding of injured tissue and for promotion of wound healing.

DESCRIPTION OF THE RELATED ART

Tissue adhesives based on fibrinogen are used for suture-free and/or suture-supporting sealing of human or animal tissue parts and/or parts of organs for wound healing, hemostasis and promotion of wound healing.

The mode of action is based on the fact that soluble fibrinogen, contained in ready-to-use liquid tissue adhesive, can be converted into insoluble fibrin by the action of thrombin and Factor XIII contained in the tissue adhesive. Factor XIII is converted to Factor XIIIa during the reaction and this crosslinks the already formed fibrin to a high polymer essential for the product's effect as a tissue adhesive. The required thrombin activity can either originate from the tissue which is to be joined (the wound surface) or can be added during adhesion to the tissue adhesive in the form of a thrombin and $Ca^{2+}$ ion-containing solution.

For hemostasis and/or tissue adhesion to take place, the following agents are used. These are based on the utilization of the last phase of the blood coagulation cascade reaction (conversion of fibrinogen into fibrin and crosslinking of fibrin by Factor XIIIa):

a) thrombin alone (as a powder, solution or in combination with an absorbent carrier, for example, a collagen fleece): such an agent triggers the coagulation of the fibrinogen present in the recipient's blood. However, the firmness of the formed clot is dependent upon the blood fibrinogen concentration which is relatively low (approximately 3 mg/ml). The hemostatic and/or adhesive effect of such preparations is therefore relatively small and/or can even be completely lacking in patients with hypofibrinogenemia.

b) tissue adhesives based on fibrinogen and Factor XIII corresponding to AT-B-359 653, AT-B-359 652 and AT-B-369 990. Such preparations have a substantially higher content of fibrinogen and Factor XIII than human blood; after the action of thrombin (in the presence of $Ca^{2+}$ ions), such preparations result in clots of high firmness and good tissue adhesiveness such that satisfactory hemostatic and adhesive effects can be achieved.

These preparations are generally used in combination with thrombin solution, wherein the solution containing fibrinogen must be mixed as quickly and completely as possible immediately before use so that an optimal effect is achieved. Therefore, a special mix and delivery device (Duploject®, Immuno AG) has also been developed for simple application.

Clinically however, there is a need for suitable preparations for hemostasis and tissue adhesion which are easier to use.

c) dry preparations in the form of absorbent fleece which contain fibrinogen and thrombin and/or substances releasing thrombin in the presence of body fluids (DE 31 05 624 and DE 32 14 337).

These preparations must be stored completely dry in order to prevent premature coagulation, some of which already occurs in the presence of trace amounts of moisture in the preparation. Consequently, such preparations are normally packaged air-tight or moisture-tight in combination with a desiccant. However, the required dryness of such preparations also causes an undesired brittleness which complicates the application to wound surfaces.

A further fundamental problem of such preparations is that upon application thrombin due to its better solubility dissolves substantially faster than the simultaneously present fibrinogen. For this reason, fibrinogen can no longer dissolve in a thrombin-containing medium. At the start of the dissolution of a fibrinogen particle, a solid fibrin layer immediately forms on its surface which inhibits the further dissolution of fibrinogen. Thus, in the best case, only a small fraction of the total amount of fibrinogen present in such a preparation can be effective.

d) Finally, a so-called one-component adhesive has also been proposed (EP-2 53 198) whose application is anticipated to be simpler in comparison to tissue adhesives corresponding to AT-359 653 and AT-359 652. According to this proposal, the application solution of such one-component adhesives contain fibrinogen, Factor XIII, a thrombin inhibitor, an increased content of prothrombin, prothrombin complex factors and calcium ions.

Preparations of this type are stable in lyophilized form. Dissolution before use should be carried out with a diluted $CaCl_2$ solution, whereupon the dissolved preparation should then more or less promptly coagulate upon application according to the $Ca^{2+}$ concentration. The true activator which finally triggers coagulation is then $CaCl_2$, not thrombin. Therefore, the calcium ion concentration must be adjusted very exactly in order to allow for dissolution before the commencement of coagulation on the one hand and on the other hand to achieve a sufficiently rapid coagulation reaction on the wound surface.

For these reasons, preparations of this type are not simpler at all, but rather even more difficult to apply than existing tissue adhesives corresponding to b). Thus, it is not surprising that preparations of this type, those according to EP 253 198, have not yet become established in the clinic.

BRIEF SUMMARY OF THE INVENTION

Therefore, the object of the present invention is to create a very effective and easy to use preparation for hemostasis, adhesion of injured tissue and promotion of wound healing without the disadvantages of existing preparations.

According to the invention, this problem is solved by a preparation, which comprises fibrinogen and an activator or pro-activator of prothrombin (present in blood) as active ingredients, which activator or pro-activator does not directly react with fibrinogen. Therewith, prothrombin present in the patient's blood is converted to thrombin, which in turn causes fibrin clot formation.

DETAILED DESCRIPTION OF THE INVENTION

The tissue adhesive according to the invention is depleted with respect to prothrombin which is less than 5 U prothrombin/g fibrinogen, preferably less than 1 U/g, and most preferably, less than the detection limit with conventional, known analytical methods. Factor Xa, produced according to DE 43 25 872 for example, is preferably used as a prothrombin activator.

Advantageously, such a preparation also comprises phospholipids, preferably associated with the activator in vesicular form, but also coagulation Factor XIII, $Ca^{2+}$ ions and/or a calcium salt, or an inhibitor of fibrinolysis which does not inhibit or only moderately inhibits the activator. Preferred fibrinolysis inhibitors are aprotinin or $\alpha_2$-plasma inhibitor.

Such a preparation can additionally comprise small amounts of an inhibitor of coagulation, for example a thrombin inhibitor such as AT-III, AT-III-heparin complex or hirudin, for improvement of storage stability.

The preparation can be presented as a liquid and/or in liquid-deep frozen form or as a lyophilisate, preferably bound to a biologically resorbable support which is water insoluble or sparingly soluble in water such as collagen fleece, fibrin foam, gelatin or cellulose, or optionally a modified form of cellulose such as oxycellulose.

Likewise, alternative supports may comprise polylactic acid, chitin, chitosan, proteoglycans, glycosaminoglycans; such as chondroitin sulfate, hyaluronic acid or keratin sulfates, heparin sulfates, dextrans, elastins, fibronectins, vitronectins, laminins, tenascins, spongiosa-bone material, preferably in decalcified form corresponding to EP-321 442, and/or hydroxylapatite.

The components of the tissue adhesive preparation are preferably isolated from human blood plasma and subjected to inactivation procedures to destroy or remove possibly present viruses. The tissue adhesive preparation itself can also be so treated, for example, by heat treatment according to EP-159 311.

The preparation may additionally comprise further active ingredients such as antibiotics, growth hormones, other plasma proteins, for example, fibronectin, as well as other coagulation factors, especially Factor V (with the exclusion of prothrombin). Activation, i.e. conversion of fibrinogen into fibrin, and crosslinking of fibrin by Factor XIIIa, first occurs following contact with blood and/or injured tissue; that is, essentially by the prothrombin present therein and optionally Factor XIII. Prothrombin is converted into thrombin by the prothrombin activator, preferably Factor Xa, contained in the preparation. Thrombin then triggers the coagulation process, i.e. the fibrinogen which is also present in the preparation as well as the fibrinogen of blood itself are converted into fibrin; Factor XIII is activated to Factor XIIIa by thrombin. This crosslinks the formed fibrin to a high polymer, whereby the firmness of the formed fibrin clot is substantially increased.

The preferred amount of activator is between the range of 0.001 to 10 U of Factor Xa or its equivalents, preferably 0.1 to 1 U/cm$^3$ of tissue adhesive. In the case of a fleece, as much prothrombin activator or pro-activator as possible is recommended so that 5 to 500 µg, preferably 10 to 100 µg, prothrombin are activated in less than 60 seconds, preferably in less than 30 seconds.

A particular feature of the preparation according to the invention is its stability, not only in a dry state but also in the presence of water and/or as a solution. Fibrinogen is activated only upon application, i.e. through contact with blood and/or wound secretion of patients, whereby a surprisingly good hemostatic and adhesive effect is obtained.

Instead of Factor Xa, other prothrombin activators or pro-activators which do not react with fibrinogen or react only very slowly can also be used, such as for example, activated coagulation factors with the exception of thrombin; among them, Factors VIIa, IXa, XIa, and XIIa but also "tissue factor". Likewise, suitable activators from suitable snake venoms or bacteria, described for example in Thromb. Haemostas. 65, 627–630 (1991), can equally be used.

The preparation can also be presented as a so-called "dry adhesive" in solid form, preferably as a thin fleece or powder. The residual water content in this preparation is not critical. Preferably, the residual water content is less than 10%, most preferably less than 5%. Such a preparation is preferably present as a thin fleece with little or no amount of water insoluble support such as collagen or fibrin. For adhesion of two (soft) tissue parts, an appropriate piece of the "dry adhesive" is applied to a wound surface and the second wound surface (the second tissue part) is subsequently adapted and shortly pressed together. The preparation promptly dissolves by means of the blood and/or wound secretion present and subsequently solidifies with the commencement of coagulation, whereby the adhering and hemostatic effect is achieved. Thereby, a solid, 2-sided adhering tissue adhesive is made available by the "dry material" according to the invention, which is especially suitable for joining soft tissue parts such as liver or spleen.

EXAMPLE 1

Collagen fleece with fibrinogen, Factor XIII, Factor Xa and phospholipids (as a phospholipid-Factor Xa complex)

1.1 Preparation

A commercially available collagen fleece (Tissue Vlies, Immuno, approx. 5 mm thick) was cut into pieces of approximately 2×2 cm and the pieces were immersed in a solution of the following composition, deep frozen and lyophilized:

| | | |
|---|---|---|
| Fibrinogen | 10 | mg/ml |
| Factor XIII | 3.5 | U/ml |
| Factor Xa | 0.13 | U/ml |
| PCPS* | 0.0025 | ml/mg |
| Human albumin | 1.5 | g/l |
| Ca$^{2+}$ | 5 | mmol/l |
| NaCl | 180 | mmol/l |
| Tris.HCl | 20 | mmol/l |
| Saccharose | 50 | mg/l |
| pH | 7.3 | |

Factor Xa and PCPS rows bracketed as: Phospholipid-Factor Xa complex

*Phosphatidylcholine + Phosphatidylserine

The active ingredients contained in the solution were produced in the following manner:

Fibrinogen:

A cryoprecipitate obtained from human citrated plasma was dissolved with a 10-fold amount of a buffer solution containing 6 g sodium citrate.2H$_2$O, 7 g NaCl, 13 g ε-aminocaprionic acid and 600 IU heparin per liter. The pH value was then adjusted to 7.3. 150 g solid glycine per 1 solution was then added during stirring and the pH value readjusted to 7.3.

The protein precipitate so formed was separated by centrifugation, dissolved again as described above. Precipitation with glycine was repeated as described above. The precipitate obtained after centrifugation was washed at a temperature between 0°–2° C. with a further buffer solution (pH 6.5) comprising 6.6 g sodium citrate.2H$_2$O, 3.4 g NaCl and 200 IU heparin per liter. The protein concentration was then adjusted to 40 g/l and the pH to 7.3. Purified human albumin (6 g/l) was next added and the solution was deep frozen and lyophilized.

For inactivation of potentially present viruses, the material was heated with a residual moisture content of 7.5% by weight for 10 hours at 60° C. and 1 hour at 80° C. The purified, lyophilized fibrinogen preparation thus obtained comprised only traces of other plasma proteins besides the added human albumin. Prothrombin remained present at a level of only 4 U/g fibrinogen.

Determination of the protein composition of a non-reduced and a reduced sample was done by SDSpolyacrylamide gel electrophoresis, staining with Coomassie-blue and densitometric analysis.

Determination of the prothrombin content was done according to the one-stage method based on the prothrombin time, according to Quick, Journal Biological Chemistry 109, p 73 (1935).

Production and testing of a purified, virus-inactivated Factor XIII concentrate was conducted according to Example 3C of European patent application EP 637 451 which is incorporated by reference.

Factor Xa was produced and tested as described in DE 43 25 872.

The production of phospholipid (PCPS)-Factor Xa complex was conducted by producing PCPS vesicles according to the extrusion method of Olsen et al., Biophysica et Biochimica Acta 557, pp 9–23, 1979 and subsequent complexing with Factor Xa. In a 100 ml flask, 40.0 mg 1,2-dioleoyl-sn-glycero-3-phosphocholine and 10.0 mg 1-palmitoyl-2-oleoyl-sn-glycero-3-phosphoserine (Avanti Polar Lipids) were dissolved in 5 ml chloroform and concentrated with the aid of a rotatory evaporator under reduced pressure and a temperature of 30° C. After complete removal of the solvent, the residual matter was maintained under vacuum at 30 mbar for over 30 minutes. The phospholipid film was subsequently hydrated by addition of 5 ml TBS buffer (20 mM Tris, 150 mM NaCl, pH 7.4) and gentle shaking for over an hour at room temperature and subsequently lyophilized. After addition of 5 ml water, the dispersion of multi-lammeller vesicles resulting therefrom was pressed ten times through two stacked 100 nm polycarbonate filters (10 ml Thermobarrel-Extruder, Lipex-Biomembranes Inc., Vancouver Canada) under pressurized $N_2$. Determination of the particle size using dynamic light scattering resulted in an average diameter of approximately 100 nm. Factor Xa (TBS-buffer) was added to the vesicle dispersion produced in this matter.

Subsequently, the $CaCl_2$ was adjusted to 5 mM, and the saccharose concentration to 5% (w/v) and the preparation lyophilized. A lyophilizate produced in this manner has a phospholipid concentration of 2.9 mg/ml as well as a Factor Xa concentration of 79 U/ml after reconstitution with the appropriate volume of $H_2O$.

1.2 Effectivness

The effectiveness, i.e. the adhering and hemostatic effect of preparations produced according to 1.1, was tested in a kidney pole resection model in rabbits. Thereby, a kidney from an experimental animal under anesthesia with ketamine and xylazine (subsequently maintained with pentobarbital) is exposed and the kidney pole is removed with a scalpel. An approximately circular, evenly heavily bleeding surface of approximately 1–1.5 cm diameter results. The test preparation was placed on the bleeding surface and lightly pressed with the finger for exactly 30 seconds and thereafter released. The adhesion of the preparation is observed and the time until the complete arrest of bleeding is measured.

Results:

The preparation prepared according to 1.1 adhered well to the heavily bleeding surface. A complete arrest of bleeding was obtained after 1 minute.

We claim:

1. A tissue adhesive, comprising a coagulation-effective amount of fibrinogen and a blood-derived activator or pro-activator of prothrombin, wherein said activator or pro-activator does not react with fibrinogen and wherein the tissue adhesive comprises less than 5 units prothrombin/g fibrinogen and is stable, wherein said adhesive clots only upon contact with tissue.

2. Tissue adhesive according to claim 1, which comprises less than 1 unit prothrombin/g fibrinogen.

3. Tissue adhesive according to claim 1, wherein said activator is Factor Xa.

4. Tissue adhesive according to claim 3, which contains 0.001 to 10 units of Factor Xa activity per $cm^3$ of tissue adhesive.

5. Tissue adhesive according to claim 1, which additionally contains an inhibitor of coagulation or fibrinolysis.

6. Tissue adhesive according to claim 5, wherein said inhibitor of coagulation is anti-thrombin III, anti-thrombin III-heparin complex or hirudin.

7. Tissue adhesive according to claim 5, wherein said inhibitor of fibrinolysis is aprotinin or alpha-2-antiplasmin.

8. Tissue adhesive according to claim 1, which additionally contains phospholipids.

9. Tissue adhesive according to claim 8, wherein said phospholipids present in vesicular form are associated with said activator or pro-activator.

10. Tissue adhesive according to claim 1, which additionally comprises Factor V.

11. Tissue adhesive according to claim 1, which additionally contains Factor XIII.

12. Tissue adhesive according to claim 11, wherein said Factor XIII is contained in an amount of at least 80 units/g fibrinogen.

13. Tissue adhesive according to claim 11, wherein said Factor XIII is contained in an amount of at least 150 units/g fibrinogen.

14. Tissue adhesive according to claim 1, wherein components of the tissue adhesive and/or the tissue adhesive itself is(are) treated for inactivation of viruses.

15. Tissue adhesive according to claim 1, further comprising fibronectin.

16. Tissue adhesive according to claim 1, which additionally comprises antibiotics, growth hormones and/or coagulation factors different from prothrombin as further active ingredients.

17. Tissue adhesive according to claim 1, which is present as a liquid preparation.

18. Tissue adhesive according to claim 17, which is present in a liquid, deep frozen form.

19. Tissue adhesive according to claim 1, which is present in solid and/or lyophilized form, preferably as a dry adhesive.

20. Tissue adhesive according to claim 1, which is applied to a biologically resorbable support which is water insoluble or sparingly soluble in water.

21. Tissue adhesive according to claim 20, wherein said support contains a collagen fleece, collagen foam, fibrin, gelatin or cellulose.

22. Tissue adhesive according to claim 1, wherein a sufficient amount of said activator or pro-activator is contained per $cm^2$ collagen fleece to activate 5 to 50 μg prothrombin in less than 60 seconds.

23. A kit for the production of a tissue adhesive according to claim 1 comprising
   (i) a tissue adhesive according to claim 1, and
   (ii) a biologically degradable, water-insoluble support.

24. Tissue adhesive according to claim 3, wherein the adhesive contains about 0.1 units of Factor Xa per $cm^3$ of tissue adhesive.

25. Tissue adhesive according to claim 1, wherein a sufficient amount of said activator or pro-activator is contained per $cm^2$ collagen fleece to activate 10 to 100 μg prothrombin in less than 60 seconds.

26. Tissue adhesive according to claim 1, wherein a sufficient amount of said activator or pro-activator is contained per cm$^2$ collagen fleece to activate 10 to 100 μg prothrombin in less than 30 seconds.

27. Tissue adhesive according to claim 1, wherein a sufficient amount of said activator or pro-activator is contained per cm$^2$ collagen fleece to activate 5 to 50 μg prothrombin in less than 30 seconds.

28. Tissue adhesive according to claim 15, further comprising a fibrinolysis inhibitor.

29. Tissue adhesive according to claim 21, wherein said cellulose is in the modified oxycellulose form.

30. A tissue adhesive according to claim 1, wherein said a coagulation-effective amount is about 10 mg/ml of fibrinogen.

31. A tissue adhesive according to claim 1, wherein said a coagulation-effective amount is an amount sufficient to arrest bleeding in about 1 minute.

32. A method of using a tissue adhesive according to claim 1 as a hemostatic, comprising applying to a wound of a patient an effective amount of said adhesive.

33. A method of hemostasis, comprising applying to a wound a tissue adhesive, wherein said adhesive comprises a coagulation-effective amount of fibrinogen and a blood-derived activator or pro-activator of prothrombin, wherein said activator or pro-activator does not react with fibrinogen and wherein the tissue adhesive comprises less than 5 units prothrombin/g fibrinogen and is stable, wherein said adhesive clots only upon contact with tissue.

34. A method according to claim 33, wherein said a coagulation-effective amount is about 10 mg/ml of fibrinogen.

35. A method according to claim 33, wherein said a coagulation-effective amount is an amount sufficient to arrest bleeding in about 1 minute.

* * * * *